United States Patent [19]

Eggertsen et al.

[11] Patent Number: 4,934,182
[45] Date of Patent: Jun. 19, 1990

[54] PROCESS AND APPARATUS FOR DETERMINING WATER CONTENT OF MATERIALS

[75] Inventors: Frank T. Eggertsen, Orinda; Loren D. Nickoley, Antioch, both of Calif.

[73] Assignee: Flink Ink Corporation, Detroit, Mich.

[21] Appl. No.: 339,400

[22] Filed: Apr. 17, 1989

[51] Int. Cl.$^5$ ............... G01N 15/08; G01N 31/00
[52] U.S. Cl. ............................. 73/73; 73/29.1; 73/38; 73/61.1 R; 422/83; 422/89; 436/39; 436/176
[58] Field of Search ............... 73/73, 29, 61.1 R, 38; 422/83, 89; 436/39, 176

[56] References Cited

U.S. PATENT DOCUMENTS

| | | | |
|---|---|---|---|
| 3,019,342 | 1/1962 | Brooke | 73/73 |
| 3,046,098 | 7/1962 | Brasseur et al. | 422/83 |
| 3,247,702 | 4/1966 | Houser et al. | 73/29 |
| 3,265,301 | 8/1966 | Amdur et al. | 73/29 |
| 3,367,850 | 2/1968 | Johnson | 422/83 |
| 3,498,110 | 3/1970 | Brun | 73/38 |
| 3,590,634 | 7/1971 | Pasternak | 73/38 |
| 3,604,246 | 9/1971 | Toren | 73/38 |
| 3,939,693 | 2/1976 | Dumont | 73/19 |
| 4,464,338 | 8/1984 | Dotson et al. | 422/78 |

OTHER PUBLICATIONS

Knight, H. S. et al., "Determination of Traces of Water in Hydrocarbons," Analytical Chemistry, vol. 34, No. 7 (Jun. 1962).

Jenke, D. R. et al., "Determination of Moisture and Volatile Content in Coal by Pressure Change and Gas Chromatography," Analytical Chemistry, vol. 54, pp. 843–845 (Apr. 1982).

Forbes, J. W., "Trace Water Determination by Infrared Spectrometry," Analytical Chemistry, vol. 37, No. 9 (Aug. 1962).

Primary Examiner—Allan N. Shoap
Assistant Examiner—Diego F. F. Gutierrez
Attorney, Agent, or Firm—Glen R. Grunewald

[57] ABSTRACT

A device and process to measure the water content of a material or the water permeability of a membrane by stably humidifying a carrier gas stream and passing it through calcium carbide to convert the water content of the stream to acetylene, then producing a spectrographic or equivalent trace establishing the stable acetylene value of the carrier gas, then passing carrier gas into contact with the material whose water content is to be measured to evaporate water from it and passing the carrier gas through the calcium carbide whereby the water content of the material is represented by the area between the stable acetylene value and the spectrographic trace caused by the added water.

5 Claims, 2 Drawing Sheets

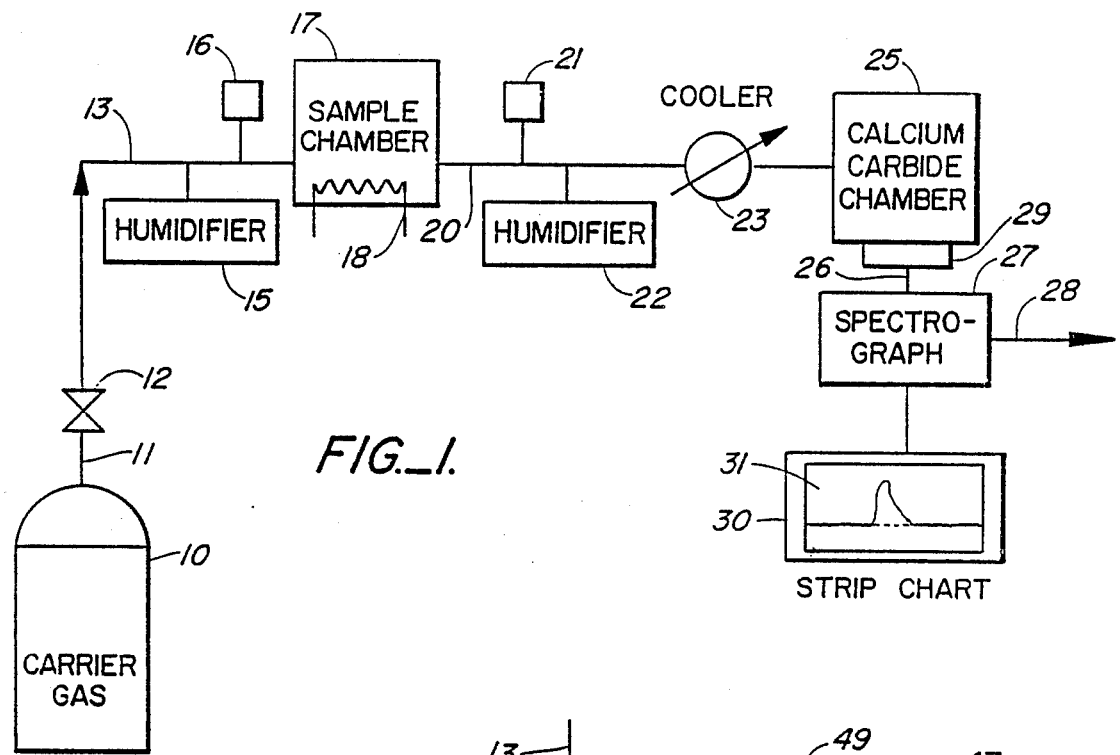
FIG._1.
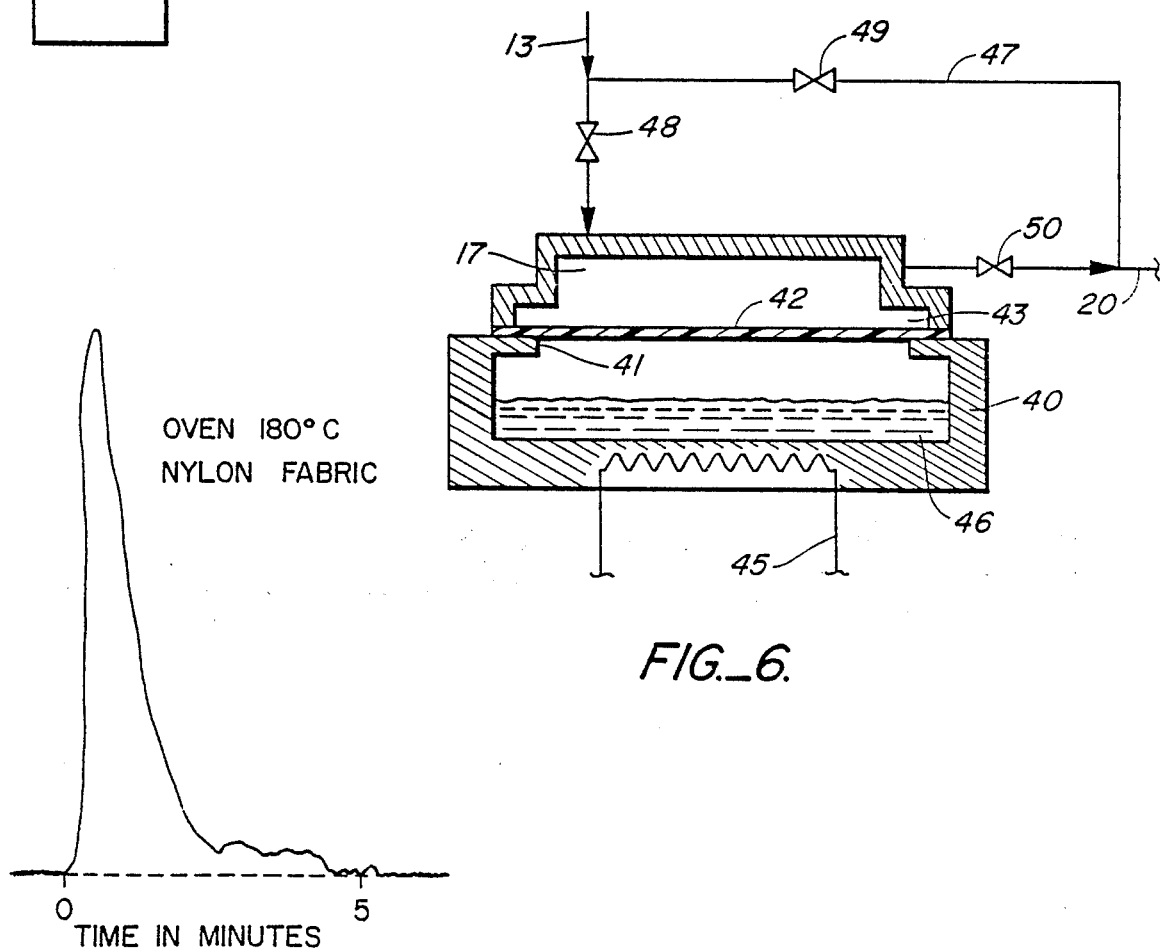
FIG._6.
OVEN 180° C
NYLON FABRIC
TIME IN MINUTES
FIG._2.

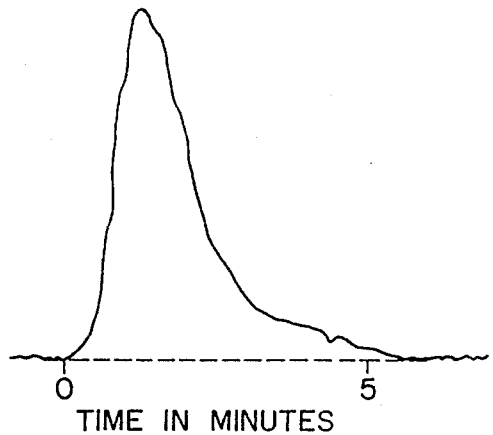
OVEN 180° C
PAPER STOCK
TIME IN MINUTES
FIG._3.
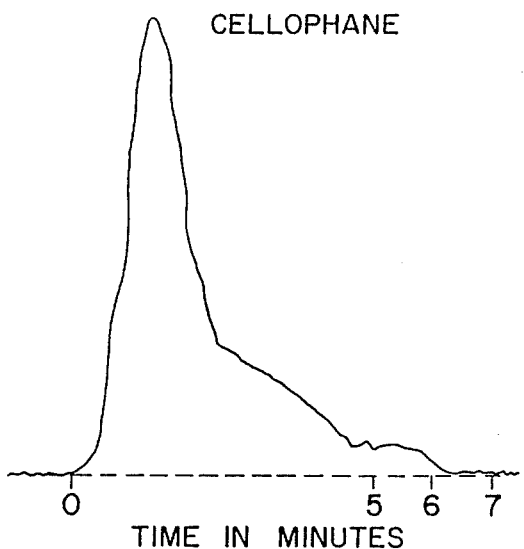
OVEN 180° C
CELLOPHANE
TIME IN MINUTES
FIG._4.
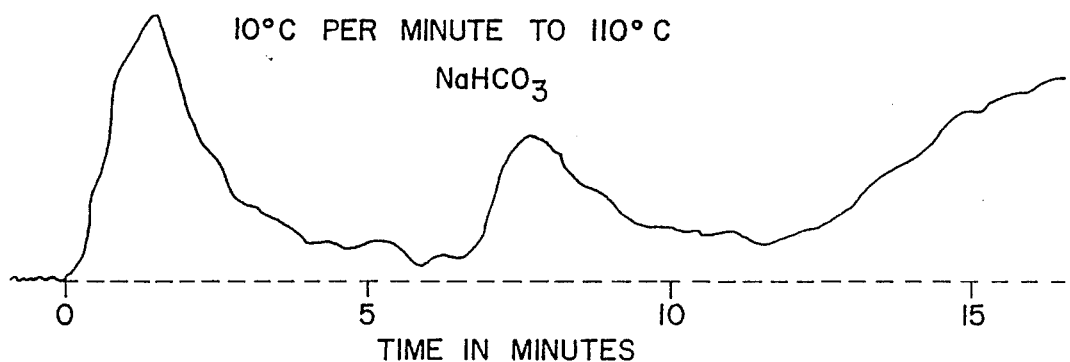
OVEN STARTS AT 40° C AND TEMPERATURE RAISED
10° C PER MINUTE TO 110° C
NaHCO₃
TIME IN MINUTES
FIG._5.
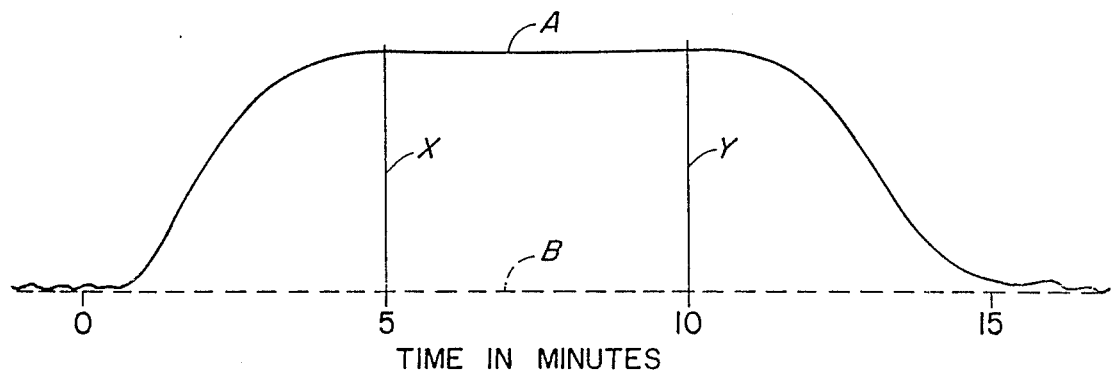
TIME IN MINUTES
FIG._7.

PROCESS AND APPARATUS FOR DETERMINING WATER CONTENT OF MATERIALS

FIELD OF THE INVENTION

This invention is in the field of analyzing materials to determine water content. It is particularly useful to determine small amounts of water.

BACKGROUND ART

It is frequently desirable or necessary to measure small amounts of water in materials. For example it is frequently necessary to determine the humidity of a gas, the amount of water in an organic liquid or solvent such as petroleum, alcohol or an oil, the amount of water in a solid such as paper, pigment, fabric or coal or the water permeability of a material such as a packaging material.

In addition to determining the free water content of a material it is also useful to determine the capillary water content. Capillary water is water that is bound in small interstices of a crystalline material or is absorbed on material in a manner such that it does not merely evaporate from the material but requires greater energy to drive it off. It is also useful to determine the water of hydration or water of crystallization of a material. Water of hydration or water of crystallization is water that is associated with molecules of salts whereby some chemical change is required to separate the water from the molecule with which it is associated.

It is also sometimes useful to measure the course of a chemical reaction where water is a reaction product. Such reactions are exemplified by carbonization of sugar, or decomposition of sodium bicarbonate into water and sodium carbonate or combustion of hydrocarbons.

It is common to analyze for the water content of a material spectrographically. A specimen to be tested has a dry carrier gas stream passed over it to evaporate the water in the specimen so that it enters the gas stream. The carrier gas stream is then analyzed spectrographically to determine the amount of water in it. This method for determining water has many problems associated with it. Among them are that water does not produce a strong spectrographic response and that the process must be performed without the possibility of water condensing or otherwise collecting in the spectrograph or in the apparatus leading to the spectrograph. It is also necessary to calibrate the spectrograph frequently to ensure that its reading accurately represents the amount of water in the gas stream passing through it. Another problem is that a spectrograph may be influenced by other materials that are similar to water which are frequently found with water. Such materials as lower alcohols, for example, will produce a spectrographic response that will influence the accuracy of a spectrograph to determine the water content of a gas stream.

The most commonly used analytic method to determine water content of a material is the Karl Fischer method which uses an alcoholic solution of iodine, sulfur dioxide and pyridine. Although the method produces accurate results the chemical basis of the method prevents its use with many materials among which are inorganic bases, carbonates, hydrogen sulfide, mercaptans and others. In addition, the reagents traditionally used in the Karl Fischer method are noxious and each material being analyzed must be dissolved in a suitable solvent that must be compatible with the Karl Fischer method of water analysis.

It is also known to analyze for water content by having the water react with calcium carbide to produce acetylene. Water reacting with calcium carbide will produce a chemically equivalent amount of acetylene and even small amounts of water react almost completely with calcium carbide. The methods known to the art that are based on acetylene production also suffer some difficulties among which are that they must be carried out with absolutely dry carrier gas and dry apparatus and that instrument calibration is extremely important so that the exact amount of acetylene produced in the carrier gas, which is the equivalent of water in the original specimen, is read.

Another problem with the known calcium carbide methods is that calcium carbide may have variable reactivity. Calcium hydroxide is one reaction product of the reaction of water and calcium carbide and at very low humidity calcium hydroxide dehydrates to calcium oxide. The observed variable activity of fresh calcium carbide may be due to the presence of some calcium hydroxide which may dehydrate in the presence of dry carrier gas, or to the presence of some calcium oxide which may hydrate in the presence of humid carrier gas. In either case the water content of the carrier gas is altered by these reactions.

One commercially available device for measuring water by conversion of water to acetylene with calcium carbide is sold under the name C-AQUA-TESTER by C. W. BRABENDER INSTRUMENTS, INC. It includes a sealed reaction chamber for the material being tested and calcium carbide, and when calcium carbide and the water in the material react to produce acetylene the water content of the material is determined by the rise in pressure in the reaction chamber. This method is slow and cumbersome because each test requires assembling and disassembling a pressure vessel, and being based on pressure, it is sensitive to temperature and the vaporization of the material being tested or the production of gas phase products by other reactions. Accordingly, it is very difficult to use to determine the water content of reactive materials, volatile liquids or solids, or of gas phase materials. The C-AQUA-TESTER is described in the article, "Determination of Moisture and Volatile Content in Coal by Pressure Change and Gas Chromatography", Jenke et al., page 843, Volume 54, No. 4, (1982), *Analytical Chemistry*.

Typical known methods to analyze for water are described in the article, "Determination of Traces of Water In Hydrocarbons"; page 749, Volume 34 (1962) *Analytical Chemistry* by Knight and Weiss, and in the article, "Trace Water Determination by Infrared Spectrometry", page 1125, Volume 34 (1962) *Analytical Chemistry*, by J. W. Forbes. Other literature of which the inventors are aware describe different methods and instruments for acetylene analysis but are no more descriptive of the concept for the process cr apparatus for acetylene analysis than the references cited above.

DISCLOSURE OF THE INVENTION

This invention is a method and device for measuring small amounts of water in a gas, a liquid or a solid, in measuring the water permeability of a membrane and in measuring the water produced by a chemical reaction. The method employs a source of calcium carbide, preferably as a cartridge that can be easily replaced, and a means for continuously measuring acetylene quantitatively. The means ay be a spectrograph or other device that is capable of continuously measuring small amounts cf acetylene in a flowing steam and recording those measurements.

The device also includes a source of carrier gas at a substantially constant humidity and a humidifier for the carrier gas that humidifies carrier gas at a substantially constant rate, a chamber for the sample or specimen to be tested and an enclosed path that starts with the source of carrier gas, passes serially through each element of the device and ends at the acetylene measuring means. The series flow includes the intermediate stations of a humidifier, a sample chamber and a calcium carbide chamber. The calcium carbide chamber must be downstream of the sample chamber and of the humidifier and it must be upstream of the means for measuring acetylene.

The sample chamber may be heated so that it is in the form of an oven that produces heat to drive moisture from the sample being tested. However, the sample chamber may be just a diaphragm through which gas may be injected if the device is used to analyze for the humidity of a gas or to confirm the response of the spectrograph to known amounts of acetylene. The sample chamber, whether in the form of an oven or not, will be made in accordance with known techniques to ensure that the sample is heated if necessary, and adequately exposed to the carrier gas so that all moisture in the sample will be incorporated into the carrier gas and thereby participate in the analysis.

BRIEF DESCRIPTION OF THE DRAWINGS

FIG. 1 is a schematic flow diagram illustrating a device embodying the invention.

FIG. 2 is an infrared trace of an analysis of the moisture content of nylon fabric.

FIG. 3 is an infrared trace of an analysis of the moisture content of paper stock.

FIG. 4 is an infrared trace of an analysis of the moisture content of cellophane.

FIG. 5 is an infrared trace of the analysis of the moisture content of sodium bicarbonate illustrating measurement of free water, bound water, and water resulting from decomposition of sodium bicarbonate.

FIG. 6 is a cross section view of a sample chamber modified to measure water permeability of a sheet material.

FIG. 7 is an infrared trace of the analysis of the water permeability of a coated paperboard packaging material

BEST MODE FOR CARRYING OUT THE INVENTION

Although the invention will be described with respect to a particular device and for particular materials it has wide application in any situation where the water content of a carrier gas can be related to the amount of water in a sample or the amount of water generated by a chemical reaction. For example, an analysis of a hydrocarbon as to relative amounts of carbon and hydrogen can be made using the process and device of this invention if that compound is completely burned and if the amounts of water and carbon dioxide in the resultant reaction product gas are independently measured and mathematically correlated. For such an analysis, the carrier gas may be air or oxygen.

Referring to FIG. 1 of the drawing, there is illustrated schematically a flow diagram showing the various elements of the device of this invention and their relationships to one another. The first element is a source of carrier gas that is illustrated as a gas bottle 10. The carrier gas may be any gas that is inert with respect to the process and equipment or appropriately reactive with the analysis being performed. Generally nitrogen has been found to be a suitable carrier for virtually any use of the process that does not involve chemical reaction. Carbon dioxide may also be a useful carrier as well as such gases as helium or other inert gases.

Carrier gas flowing from a source such as gas bottle 10 has substantially constant absolute humidity whether it is the first gas flowing from the bottle or the last. It may be desirable to pass the carrier gas flowing from the gas bottle through a drier as it passes from the bottle. If a carrier gas source such as a compressor is used, its humidity will have to be adjusted by methods known to the art so that it will have a constant absolute humidity throughcut an analysis. The device of this invention is mostly useful for analysis of small samples so the use of a gas bottle for a source of carrier gas is preferred.

The carrier gas is removed from the source 10 through line 11 which discharges through a flow control valve 12 into line 13. Line 13 is provided with a humidifier 15 that may be used or not at the option of the operator of the process. If humidifier 15 is not used, then humidifier 22 to be described hereinafter must be used in that the process requires a stable source of water from an element that is generally designated a humidifier. The humidifiers 15 and 22 may be any recognized devices for introducing water, whether in known quantity or not, into the flowing carrier gas stream at a constant rate. It has been found that a vessel containing water and having a wick extending into or close to the flowing carrier gas stream is an adequate humidifier. The humidifier may be quite simple. A test tube containing water at room temperature having a pipe cleaner extending from the water and exposed to the flow path of carrier gas has been used with success. The humidifier will usually be in the position of humidifier 15 but may be in the position of humidifier 22 if the sample in chamber 17 is sensitive to water or if very low humidity is required for the analysis. The humidifier must introduce water into the carrier gas at a constant rate and at a rate that is low enough to maintain the carrier gas humidity substantially below the saturation humidity.

A gas introducing means 16 may open into line 13. Means 16 is sealed with a diaphragm through which gas may be injected. The means 16 is employed only when the device is used to detect the water content of the injected gas or to calibrate the device. Means 16 may embody other devices to add a measured volume of gas to the carrier gas, such as a gas sample loop.

Line 13 eventually discharges into sample chamber 17. Sample chamber 17 may be an oven and in that case it will be provided with heating means 18. It is evident that if the device of this invention is going to be used entirely for analyzing the moisture content of gases, then the sample chamber is means 16 and a separate sample chamber or oven is not needed.

The carrier gas emerging from sample chamber 17 contains moisture picked up from the sample being analyzed and it passes into line 20. Line 20, in the illustrated embodiment, also includes a means 21 which is or may be identical to the means 16, and humidifier 22 which is or may be identical with the humidifier 15. Means 21 and humidifier 22 are shown in FIG. 1 to illustrate that the relative positions of the gas introduction means, the humidifier, and the sample chamber are alternative. Specifically, for some purposes it is desirable to have the humidifier upstream of the sample chamber and for other purposes it is desirable to have the humidifier downstream of the sample chamber. In the illustrated embodiment either humidifier 15 or humidifier 22 may be employed but rarely will both be employed. The same is true of gas introduction means 16 and 21.

Line 20 is illustrated a passing through cooler 23 which is another optional piece of equipment. If sample chamber 17 is operated at a temperature so high that it would interfere with the reaction between water and calcium carbide or would cause damage to the equipment, then it is within the scope of the invention to cool the gas stream emerging from sample chamber 17 before it is passed into calcium carbide chamber 25.

The carrier gas passing through line 20 is introduced into calcium carbide chamber 25. In chamber 25 all of the water in the carrier gas reacts with calcium carbide to form acetylene and calcium hydroxide. Known techniques are employed to prevent the results of the analysis from being disrupted by using spent calcium carbide.

The carrier gas flowing from chamber 25 through line 26 will contain no water. Instead, it will contain acetylene in an amount that is chemically equivalent to the amount of water in the carrier gas flowing through line 20. The carrier gas in line 26 flows through spectrograph 27 and is ultimately discharged from the device through line 28. Spectrograph 27 is connected to means 30 which produces a strip chart 31 that records a trace that corresponds to the amount of acetylene passing through spectrograph 27.

For some purposes it may be desirable to clean the gas in line 26 before it is spectrographically analyzed and for that purpose cleaner 29 is, optionally, provided. Cleaner 29 may be a column of gas chromatographic packing or other absorbent material, a condenser, a filter or other means to remove easily condensed gas, small droplets, particles or readily absorbed impurities from the carrier gas. Cleaner 29 may be integrated with or separate from calcium carbide chamber 25.

To use the device of this invention, particularly the one illustrated in FIG. 1, a carrier gas is caused to flow from bottle 10 through the device for a sufficient period of time to "season" the device. Seasoning will normally be accomplished with either humidifier 15 or humidifier 22 functioning. The seasoning process causes any unstable condition characteristic of the equipment to correct itself. It may be involved with desorbing molecules absorbed to the interior of various components of the system, to drive moisture out of the system, to deplete solvents or oils that are exposed to the flowing gas stream and to bring the flowing gas stream to equilibrium with its surroundings at the humidity and other conditions at which the carrier gas passes through the device. The seasoning process ordinarily takes just a few minutes.

As a result of the seasoning procedure the calcium carbide, and whatever calcium oxide is present in it, are brought to equilibrium with the moisture content of the carrier gas to produce a stable acetylene content in the carrier gas stream. Spectrograph 27 will respond to the acetylene production by detecting both its presence and its quantity. Strip chart 31 will register a substantially horizontal line representative of the amount of acetylene produced by the stable moisture content of the carrier gas at the stable condition of the seasoned equipment and calcium carbide. For purposes of analysis, the horizontal line or base line which represents that amount of calcium carbide can be considered zero. It is an important element of this invention that the zero line of the strip chart represents a stable water content of the carrier gas and that accurate analyses can be made even though the stable quantity of water in the carrier gas is not known. In other words, as long as the humidity of the carrier gas is constant, the absolute value of the humidity is of no significance to the accuracy or effectiveness of the process or the device of this invention for carrying it out. The stable moisture content of the carrier gas should be well below saturation to maintain a sufficient driving force to evaporate all of the water in the sample.

When the acetylene content of the carrier gas entering spectrograph 27 stabilizes so that the strip chart 31 shows a substantially horizontal line, the sample to be analyzed is introduced into sample chamber 17, or alternatively through means 16 or 21. As the carrier gas either incorporates a gas introduced through 16 or 21, or as the carrier gas takes up moisture from a solid or liquid sample in chamber 17 or water permeating a membrane, its moisture content will rise. When carrier gas including moisture from the sample being analyzed passes through chamber 25 the added moisture will also react with calcium carbide and as a result the amount of acetylene passing through line 26 and into spectrograph 27 will increase. This increase in acetylene is represented by a curve on strip chart 31 that deviates from the base line for the moisture content of the carrier gas. When the curve on strip chart 31 again coincides with the base line, all the moisture will have been extracted from the sample. The amount of moisture in the sample can then be readily calculated in that it is exactly represented by the area between the base line and the curve that deviated from the base line. This quantity may be obtained readily by graphically integrating that area on strip chart 31 using known integrating devices or by doing it manually.

The device of this invention operated as described above has many advantages. Perhaps the most important advantage is that it is not necessary to calibrate spectrograph 27 absolutely. The amount of water in the sample is equivalent to the amount of acetylene sensed above the base line acetylene content of the carrier gas. That amount is equivalent to the moisture content of the carrier gas after taking up the water in the sample to be tested. Thus, the spectrograph establishes a zero setting for itself and the only calibration necessary is to determine the amount of water necessary to produce a known increment of deviation on the strip chart 31. The analysis is based on the difference between two values and is not dependent on the absolute value of either. The difference between these two values is always accurate even if the absolute value of neither value is known.

Another advantage of the device of this invention is that the calcium carbide chamber may act as a filter to remove interfering materials from the gas stream that is analyzed. For example, if the calcium carbide chamber is maintained at a temperature cool enough to condense water, alcohol and some hydrocarbons, the alcohol and hydrocarbons will simply collect in chamber 25 but the water, whether in the vapor phase or liquid phase, will react with calcium carbide to produce its equivalent amount of gas phase acetylene in line 26.

Another advantage of this invention is that the base water content of the humidified carrier gas will prevent dehydration of any calcium hydroxide in the calcium carbide chamber thereby preventing a source of inaccuracy in the analysis caused by formation of calcium oxide.

Although the process has been described with regard to specific elements, equivalent or even improved elements may be substituted for those described. For example, any means for continuously detecting acetylene may be employed in place of spectrograph 27. Means such as flame ionization detectors may be employed with equivalent results.

A number of tests were performed to determine the accuracy of water analysis in accordance with this invention. In all of the tests a known quantity of water was added to a material and the material was analyzed for water using the device and the process of this invention. In all cases, the material tested was a liquid to avoid the difficulty of adding known quantities of water to a gas or a solid. In all cases the starting material employed was as anhydrous as possible for the conditions and equipment normally found in a laboratory. The results of these tests are set forth in the following table.

TABLE I

| Water added | Water Found % | | | |
|---|---|---|---|---|
| % | Acetone | Methanol | DOP* | Oil Based Ink |
| 0 | 0.3 | 0.3 | — | 0 |
| 1 | 1.0 | 0.8 | 0.7 | 0.7 |
| 2 | — | 2.3 | — | 1.5 |
| 3 | — | — | 2.9 | — |
| 5 | — | 4.9 | — | 5.0 |
| 8 | — | — | 6.9 | — |
| 10 | 9.0 | 11.3 | 9.6 | 10.0 |
| 20 | — | 22.3 | — | 21.0 |
| 50 | — | 48.3 | — | — |

*Dioctylphthalate dispersed in 10% methanol and 5% Igepal

A number of tests were performed using the device and process of this invention and the results of these tests are illustrated in the drawings. FIG. 2 is a trace from a strip chart that was obtained in a test to determine the moisture content of nylon fabric. Fresh calcium carbide having a grain size between 16 and 35 mesh was placed in a 4 mm I.D. tube and held in place with glass wool. The nylon fabric was at uncontrolled ambient conditions prior to the test. The apparatus and the calcium carbide were seasoned with a carrier gas that was humidified with a wick in the form of a pipe cleaner that extended from a vial of water at room temperature into the side branch of stainless steel tee through which carrier gas flowed. The pipe cleaner was positioned with its end about one inch short of the run branches of the tee through which carrier gas was flowing. The carrier gas flowed through the stainless steel tee for a period of time long enough to produce the trace to the left of zero time in FIG. 2. The trace was substantially a horizontal line that formed the base line for the analysis. A 20.7 milligram sample of the nylon material was placed in the sample chamber 17 supported on a stainless steel probe having a screen on which the sample was placed at time zero. The sample chamber was a stainless steel tube 0.25 inches in diameter enclosed in an oven. Before the sample was introduced into chamber 17 the chamber was heated to a temperature of 180° C. and a steady nitrogen flow rate of 120 cc per minute was established.

The test was begun by inserting the sample into chamber 17. The test was conducted for five minutes after which time the trace produced by the water evaporated from the nylon fabric superimposed the base line thereby indicating that all of the moisture in the nylon fabric had been evaporated. The area under the curve and above the base line represented the amount of water in the nylon fabric, which was calculated to be 3.0%.

FIG. 3 illustrates a trace to measure the amount of moisture in paper stock. The test in FIG. 3 was accomplished exactly as the test in FIG. 2 with the oven at 180° C. and the seasoning and sample introduction procedures identical. The paper specimen weighed 9.5 milligrams and the integration of the area between the base line and curve in FIG. 3 indicated that the moisture content of the paper was 5.3%.

FIG. 4 represents a trace obtained using the process and device of this invention to analyze for the moisture content of a specimen of cellophane. The process was performed at 180° C. and under conditions identical with those that produced the traces of FIGS. 2 and 3. After approximately six minutes the trace on the strip chart returned to the base line. Integration of the area between the trace and the base line indicated that the moisture content of the cellophane was 9.2%.

FIG. 5 illustrates the use of this invention for analyzing for water of different types. The process and apparatus was employed to analyze for the moisture content of sodium bicarbonate which contains three types of water. Sodium bicarbonate contains free water which simply evaporates from the surface of the material, it contains bound water which is held adsorptively to the crystals and must be driven from their absorptive contact with greater energy, and finally sodium bicarbonate decomposes to sodium carbonate and water at a temperature of about 110° C.

The test was conducted the same as the other tests reported except that the furnace temperature was maintained at 30° C. until the sample of 104 milligrams was put into it. At that point the temperature of the furnace was raised at the rate of 10° C. per minute until it reached 110° C. where it was held until the procedure was completed. The trace illustrated in FIG. 5 shows a separate curve for each type of water. At time zero of the test there was the characteristic rapid rise in acetylene content in the carrier gas which later peaked and began diminishing until it closely approached the base line at about six minutes. That characteristic curve, if carried to completion, would intersect the base line shortly after six minutes and would represent the amount of free water in the sample. Integration of the area under the curve to the point where it changed direction and started rising again indicated that the free moisture content of the sodium bicarbonate sample was 0.53%. At the point where the trace began rising again the bound water held by adsorption to the sodium bicarbonate crystal was being driven off. The resultant curve has the characteristic shape of the other curves produced by the process of this invention. The area under the curve representing bound water content was integrated and it indicated that there was about 0.33% bound water in the sample.

The third rise in the acetylene content of the carrier gas, starting at about twelve minutes, represents the water that was produced by the decomposition of sodium bicarbonate to form sodium carbonate and water. This reaction was not carried to completion because it was not useful to measure the large amount of water evolved by the decomposition reaction. Nevertheless, the three distinct peaks of the curve at the temperatures at which they occurred indicate that the device and the process of this invention are useful to measure water associated with materials in different ways.

FIG. 6 is a representation of sample chamber 17 modified for analysis of the water permeability of a sheet material. Sample chamber 17 is an open-bottom housing adapted to seal against the open top 41 of humidity chamber 40 with a specimen of sheet material 42 positioned between open bottom 43 of sample chamber 17 and humidity chamber 40. Humidity chamber 40 has a heater 45 to maintain aqueous liquid 46 at an elevated temperature.

Lines 13 and 20 provide carrier gas flow through sample chamber 17 so that moisture permeating sheet material 42 is picked up and passed to calcium carbide chamber 25 as illustrated in FIG. 1. A bypass 47 may be used by appropriately setting valves 48, 49 and 50 to initiate and discontinue the flow of carrier gas through chamber 17.

The composition and temperature of liquid 46 will determine the humidity to which sheet material 42 is exposed. Means known to the art, such as a threaded connection, a flanged connection or the like are employed to form an adequate seal between chamber 17 and chamber 40 to exclude ambient air from the interior of either.

FIG. 7 illustrates a curve obtained in a test to determine the water permeability of a membrane, specifically a coated paperboard material that was tested for water permeability to determine its utility as a packaging material.

The test was conducted using the apparatus of FIG. 6.

A saturated aqueous solution of zinc sulfate heptahydrate was placed in the humidity chamber 40 and a coated paperboard sample 40 was assembled in the apparatus as illustrated in FIG. 6. The solution was heated to 100° F. It is known that a saturated zinc sulfate solution maintained at 100° F. will produce an atmosphere above the solution surface having relative humidity of 90.

The apparatus was seasoned with carrier gas passing through bypass 47 and humidifier 22 operating. Chamber 40 was maintained at 100° F. Seasoning continued until a substantially horizontal base line trace appeared on the chart. At that point valves 48 and 50 were opened and valve 49 closed to put bypass 47 out of operation and to cause carrier gas to flow through chamber 17. After a short period of time the trace on the strip chart rose above the base line, climbing to a stable level indicated by a trace parallel to the base line and spaced above it. The base line and the trace above it are illustrated in FIG. 7.

The area between the base line B and the parallel trace A is the water permeability of the membrane being tested. The permeability was determined by integrating the area between vertical lines X and Y and between the base line B and trace A of FIG. 7 and dividing that area by the time interval X-Y which in this case was five minutes. If a number of permeability tests are to be performed using the same equipment the entire calculation is not necessary because the vertical distance between trace A and base line B can be calibrated to read permeability directly. The membrane permeability analysis described above can be performed so quickly and inexpensively that it lends itself to quality control inspection as well as laboratory analysis.

Table II reports tests to determine the water permeability of a number of sheet materials useful for packaging. All of the paper board materials were coated with a film of ink-like material which contributed to their resistance to water permeability. The conditions of the test were much more severe than one would expect to find in use, i.e. a temperature of 100° F. and relative humidity of 90.

TABLE II

| SHEET MATERIAL | PERMEABILITY (grams/100 sq. in/day) |
| --- | --- |
| Mylar (film A) | 0.5 |
| Mylar (film B) | 1.7 |
| Mylar (film C) | 7.2 |
| Coated paperboard (A) | 5.6 |
| Coated paperboard (B) | 23.9 |

We claim:
1. An apparatus to measure the water content of a material comprising:
   (a) a source of carrier gas having stable hunidity,
   (b) means to regulate the flow of said carrier gas to provide a substantially constant rate of carrier gas flow,
   (c) a material sample chamber having an inlet for carrier gas, an outlet for carrier gas and means to provide contact between said carrier gas and said material,
   (d) a humidifier including means to introduce water into said carrier gas at a substantially constant rate,
   (e) a calcium carbide chamber including an inlet for humidified carrier gas, an outlet for carrier gas and means to provide contact between humidified carrier gas and calcium carbide whereby a reaction between water and calcium forms acetylene,
   (f) means to measure the quantity of acetylene in said carrier gas,
   connected in series flow with said sample chamber and said humidifier downstream of said source of carrier gas and upstream of said calcium carbode chamber, and said calcium carbide chamber upstream of said means to measure acetylene.

2. The apparatus of claim 1 wherein said material sample chamber includes heating means.

3. The apparatus of claim 2 including a cooler in series flow between said sample chamber and said calcium carbide chamber.

4. A process for determining the water content of a material comprising:
   establishing a substantially constant flow of a carrier gas having stable humidity, said carrier gas flowing through a sample chamber, a calcium carbide chamber and means to measure acetylene content of said carrier gas continuously,
   humidifying said flowing carrier gas at a substantially constant rate to a stable absolute humidity substantially lower than the saturation humidity of said carrier gas,
   passing the resultant humidified carrier gas into reactive contact with calcium carbide to produce an acetylene-containing carrier gas,
   passing said acetylene-containing carrier gas to means to continuously measure and record acetylene content of said carrier gas to establish a base acetylene level reading, introducing said material into said sample chamber under conditions to incorporate the water in said material into said carrier gas, thereby producing carrier gas having a higher absolute humidity than said stable absolute humidity, passing the carrier gas having humidity higher than said stable absolute humidity serially into reactive contact with calcium carbide and through said means to measure acetylene content to produce an acetylene level reading higher than said base acetylene level reading, integrating the area between said base acetylene reading and said reading higher than said base acetylene reading, whereby the water content of said material is determined as said total difference.

5. A process for determining the water permeability of a membrane comprising:

establishing a substantially constant flow of a carrier gas having stable humidity, said carrier gas flowing serially through a sample chamber, a calcium carbide chamber and means to measure acetylene content of said carrier gas continuously, humidifying said flowing carrier gas at a substantially constant rate as it flows between said sample chamber and said calcium carbide chamber, passing the resultant humidified carrier gas into reactive contact with calcium carbide to produce an acetylene-containing carrier gas, passing said acetylene-containing carrying carrier gas to means to continuously measure and record acetylene content of said carrier gas to establish a base acetylene level reading, introducing said membrane into said chamber, said membrane sealing an opening between a gas at known relative humidity and the interior of said sample chamber whereby water permeating said membrane evaporates into said carrier gas to raise the absolute humidity of said carrier gas to a higher absolute humidity than said stable absolute humidity, passing the carrier gas having humidity higher than said stable absolute humidity serially into reactive contact with calcium carbide and through said means to measure acetylene content to produce an acetylene level reading higher than said base acetylene level reading, integrating the area between said base acetylene reading and said reading higher than said base acetylene reading for a time interval whereby the water permeability of said membrane for that time interval is determined as the water equivalent of said acetylene.

\* \* \* \* \*

UNITED STATES PATENT AND TRADEMARK OFFICE
CERTIFICATE OF CORRECTION

PATENT NO. : 4,934,182
DATED : June 19, 1990
INVENTOR(S) : Frank T. Eggertsen and Loren D. Nickoley It is certified that error appears in the above-identified patent and that said Letters Patent is hereby corrected as shown below:

Column 2, line 59, "cr" should be --or--.
Column 3, line 2, "ay" should be --may--.
Column 3, line 4, "cf" should be --of--.
Column 4, line 19, "throughcut" should be --throughout--.
Column 5, line 10, "a" should be --as--.
Column 7, line 52, after "branch of" insert --a--.
Column 10, line 23, "hunidity" should be --humidity--.
Column 10, line 38, after "water and calcium" insert --carbide--.
Column 10, line 43, "carbode" should be --carbide--.

Signed and Sealed this

Fourteenth Day of May, 1991

Attest:

HARRY F. MANBECK, JR.

*Attesting Officer*     *Commissioner of Patents and Trademarks*